US006582691B1

(12) United States Patent
Gallert et al.

(10) Patent No.: US 6,582,691 B1
(45) Date of Patent: Jun. 24, 2003

(54) EXPRESSION VECTOR FOR THE PRODUCTION OF DEAD PROTEINS

(75) Inventors: Karl-Christian Gallert, Karben (DE); Stefan Müllner, Lagenfeld (DE); Christoph Hüls, Wackernheim (DE); Britta Böhnisch, Ginsheim-Gustavsburg (DE)

(73) Assignee: Aventis Research & Technologies GmbH & Co., Frankfurt am Main (DE)

( * ) Notice: Subject to any disclaimer, the term of this patent is extended or adjusted under 35 U.S.C. 154(b) by 0 days.

(21) Appl. No.: 09/601,537

(22) PCT Filed: Feb. 9, 1999

(86) PCT No.: PCT/EP99/00829

§ 371 (c)(1),
(2), (4) Date: Sep. 29, 2000

(87) PCT Pub. No.: WO99/41390

PCT Pub. Date: Aug. 19, 1999

(30) Foreign Application Priority Data

Feb. 12, 1998 (DE) .......................................... 198 05 781

(51) Int. Cl.$^7$ ..................... A61K 48/00; C12N 15/866; C12N 15/63; C12P 21/00
(52) U.S. Cl. .................... 424/93.2; 424/93.1; 424/93.6; 435/320.1; 435/455; 435/456; 435/457; 435/69.1; 435/325; 435/348; 536/23.1; 536/23.2; 536/23.5; 536/24.1

(58) Field of Search ............................... 435/320.1, 455, 435/456, 457, 69.1, 325, 348; 536/23.1, 23.2, 23.5, 24.1; 424/93.1, 93.2, 93.6

(56) References Cited

U.S. PATENT DOCUMENTS 5,186,933 A  *  2/1993  Estes ........................... 424/89

FOREIGN PATENT DOCUMENTS

EP      0 778 347 A2    6/1997
WO     WO 96/18157     9/1993

OTHER PUBLICATIONS

Dangel et al., "Human Helicase Gene SKI2W in the HLA Class III Region Exhibits Striking Structural Similarities to the Yeast Antiviral Gene SKI2 and to the Human Gene KIAA0052: Emergence of a New Gene Family," *Nucleic Acids Research* 23:2120–2126 (1995).
Lee et al., "Human RNA Helicase A is Homologous to the Maleless Protein of Drosophila," *J. Biol. Chem.* 268:16822–16830 (1993).
Invitrogen Homepage (pBlueBac2).
Pharmingen Homepage (pAcG2T).

* cited by examiner

*Primary Examiner*—David Guzo
(74) *Attorney, Agent, or Firm*—Clark & Elbing LLP

(57) ABSTRACT

The invention relates to an insect cell vector for the production of proteins from the DEAD protein family.

37 Claims, 9 Drawing Sheets

```
DEAD PROTEIN SUPERFAMILY

ATPase A Motif                              ATPase B Motif
NH2------AXXXGKT-----PTRELA-----GG-----TPGR-----DEAD-----SAT----FXXXT----
    21-299          24-42      22-28  19-27  19-22     27-51   59-70    52-53

RGXD-----HRIGRXXR-----COOH
    20         24-236 e1F-4A
NH2-----AXXXXGKT-----PTRELA-----GG-----TPGR-----DEAD-----SAT----FINT----
     75           24           22    20      20      27      62      52

RGID-----HRIGRXXR-----COOH
    20         41

DEAH SUBFAMILY

NH2-----GXXXXGKT-----RVAA-----XX-----TDGX-----DEAH-----SAT----FXT------
   245-505        22-24       29    7-8      19       28     58-61   75-84

XGXX-----QRIGRXGR-----COOH
    25         315-373

DEXH SUBFAMILY

NH2-----XXXXXGKT-----PTRXXX-------------------------------DEXH-----TAT----FXXS---
   81-1904         19-27           55-60                         24-30  44-72   46-55

XGXX-----QRXGRXGR-----COOH
   38-44       155-1799
```

Fig. 1

```
BamH I  Rsr II  BssH II EcoR I   Stu I   Sal I Sst I  Spe I
GGATCCCGGTCCGAAGCGCGCGGAATTCAAAGGCCTACGTCGACGAGCTCACTAGTCGC

Not I   Nsp V  Xba I   Pst I   Xho I Sph I  Kpn I Hind III
GGCCGCTTTCGAATCTAGAGCCTGCAGTCTCGAGGCATGCGGTACCAAGCTT
```

Fig. 4B

FULL-LENGTH-Clone

SR-DOMAIN

Clone D1: C-TERMINAL DELETION

Clone D2: INTERNAL CONTROL FRAGMENT

Eco RI (1144)    Not I (1588)

SEQUENCE LISTING

```
<160> NUMBER OF SEQ ID NOS: 29

<210> SEQ ID NO 1
<211> LENGTH: 6
<212> TYPE: PRT
<213> ORGANISM: Artificial Sequence
<220> FEATURE:
<223> OTHER INFORMATION: Thrombin Cleavage Site

<400> SEQUENCE: 1

Leu Val Pro Arg Gly Ser
 1               5

<210> SEQ ID NO 2
<211> LENGTH: 4
<212> TYPE: PRT
<213> ORGANISM: Artificial Sequence
<220> FEATURE:
<223> OTHER INFORMATION: Factor Xa Cleavage Site

<400> SEQUENCE: 2

Ile Glu Gly Arg
 1

<210> SEQ ID NO 3
<211> LENGTH: 32
<212> TYPE: DNA
<213> ORGANISM: Artificial Sequence
<220> FEATURE:
<223> OTHER INFORMATION: Oligonucleotide primer

<400> SEQUENCE: 3
atgaattcgg ggacaccagt gaggatgcct cg                              32

<210> SEQ ID NO 4
<211> LENGTH: 27
<212> TYPE: DNA
<213> ORGANISM: Artificial Sequence
<220> FEATURE:
<223> OTHER INFORMATION: Oligonucleotide primer
```

<400> SEQUENCE: 4
ccgataatgt ctgtctttcc ggatatt                                    27

<210> SEQ ID NO 5
<211> LENGTH: 40
<212> TYPE: DNA
<213> ORGANISM: Artificial Sequence
<220> FEATURE:
<223> OTHER INFORMATION: Oligonucleotide primer

<400> SEQUENCE: 5
tgacagtcgg acttagtcct aacgccggcg atatgcatgc                      40

<210> SEQ ID NO 6
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 6
gcctctgcca tggaggagga gatg                                       24

<210> SEQ ID NO 7
<211> LENGTH: 1226
<212> TYPE: PRT
<213> ORGANISM: Homo sapiens

<400> SEQUENCE: 7

```
Met Gly Asp Thr Ser Glu Asp Ala Ser Ile His Arg Leu Glu Gly Thr
 1               5                  10                  15

Asp Leu Asp Cys Gln Val Gly Gly Leu Ile Cys Lys Ser Lys Ser Ala
             20                  25                  30

Ala Ser Glu Gln His Val Phe Lys Ala Pro Ala Pro Arg Pro Ser Leu
         35                  40                  45

Leu Gly Leu Asp Leu Leu Ala Ser Leu Lys Arg Glu Arg Glu Glu
     50                  55                  60

Lys Asp Asp Gly Glu Asp Lys Lys Ser Lys Val Ser Ser Tyr Lys
65                  70                  75                  80

Asp Trp Glu Glu Ser Lys Asp Gln Lys Asp Ala Glu Glu Gly
             85                  90                  95

Gly Asp Gln Ala Gly Gln Asn Ile Arg Lys Asp Arg His Tyr Arg Ser
            100                 105                 110

Ala Arg Val Glu Thr Pro Ser His Pro Gly Gly Val Ser Glu Glu Phe
        115                 120                 125

Trp Glu Arg Ser Arg Gln Arg Glu Arg Glu Arg Glu His Gly Val
    130                 135                 140

Tyr Ala Ser Ser Lys Glu Glu Lys Asp Trp Lys Lys Glu Lys Ser Arg
145                 150                 155                 160

Asp Arg Asp Tyr Asp Arg Lys Arg Asp Arg Asp Glu Arg Asp Arg Ser
                165                 170                 175

Arg His Ser Ser Arg Ser Glu Arg Asp Gly Gly Ser Glu Arg Ser Ser
            180                 185                 190

Arg Arg Asn Glu Pro Glu Ser Pro Arg His Arg Pro Lys Asp Ala Ala
        195                 200                 205

Thr Pro Ser Arg Ser Thr Trp Glu Glu Glu Asp Ser Gly Tyr Gly Ser
    210                 215                 220
```

-continued

```
Ser Arg Arg Ser Gln Trp Glu Ser Pro Ser Pro Thr Pro Ser Tyr Arg
225                 230                 235                 240

Asp Ser Glu Arg Ser His Arg Leu Ser Thr Arg Asp Arg Asp Arg Ser
            245                 250                 255

Val Arg Gly Lys Tyr Ser Asp Asp Thr Pro Leu Pro Thr Pro Ser Tyr
                260                 265                 270

Lys Tyr Asn Glu Trp Ala Asp Asp Arg Arg His Leu Gly Ser Thr Pro
            275                 280                 285

Arg Leu Ser Arg Gly Arg Gly Arg Arg Glu Glu Gly Glu Glu Gly Ile
            290                 295                 300

Ser Phe Asp Thr Glu Glu Glu Arg Gln Gln Trp Glu Asp Asp Gln Arg
305                 310                 315                 320

Gln Ala Asp Arg Asp Trp Tyr Met Met Asp Glu Gly Tyr Asp Glu Phe
                325                 330                 335

His Asn Pro Leu Ala Tyr Ser Ser Glu Asp Tyr Val Arg Arg Arg Glu
                340                 345                 350

Gln His Leu His Lys Gln Lys Gln Lys Arg Ile Ser Ala Gln Arg Arg
            355                 360                 365

Gln Ile Asn Glu Asp Asn Glu Arg Trp Glu Thr Asn Arg Met Leu Thr
370                 375                 380

Ser Gly Val Val His Arg Leu Glu Val Asp Glu Asp Phe Glu Glu Asp
385                 390                 395                 400

Asn Ala Ala Lys Val His Leu Met Val His Asn Leu Val Pro Pro Phe
                405                 410                 415

Leu Asp Gly Arg Ile Val Phe Thr Lys Gln Pro Glu Pro Val Ile Pro
            420                 425                 430

Val Lys Asp Ala Thr Ser Asp Leu Ala Ile Ile Ala Arg Lys Gly Ser
            435                 440                 445

Gln Thr Val Arg Lys His Arg Glu Gln Lys Glu Arg Lys Lys Ala Gln
    450                 455                 460

His Lys His Trp Glu Leu Ala Gly Thr Lys Leu Gly Asp Ile Met Gly
465                 470                 475                 480

Val Lys Lys Glu Glu Glu Pro Asp Lys Ala Val Thr Glu Asp Gly Lys
                485                 490                 495

Val Asp Tyr Arg Thr Glu Gln Lys Phe Ala Asp His Met Lys Arg Lys
            500                 505                 510

Ser Glu Ala Ser Ser Glu Phe Ala Lys Lys Lys Ser Ile Leu Glu Gln
            515                 520                 525

Arg Gln Tyr Leu Pro Ile Phe Ala Val Gln Gln Glu Leu Leu Thr Ile
    530                 535                 540

Ile Arg Asp Asn Ser Ile Val Ile Val Val Gly Glu Thr Gly Ser Gly
545                 550                 555                 560

Lys Thr Thr Gln Leu Thr Gln Tyr Leu His Glu Asp Gly Tyr Thr Asp
                565                 570                 575

Tyr Gly Met Ile Gly Cys Thr Gln Pro Arg Arg Val Ala Ala Met Ser
            580                 585                 590

Val Ala Lys Arg Val Ser Glu Glu Met Gly Gly Asn Leu Gly Glu Glu
            595                 600                 605

Val Gly Tyr Ala Ile Arg Phe Glu Asp Cys Thr Ser Glu Asn Thr Leu
            610                 615                 620

Ile Lys Tyr Met Thr Asp Gly Ile Leu Leu Arg Glu Ser Leu Arg Glu
625                 630                 635                 640

Ala Asp Leu Asp His Tyr Ser Ala Ile Ile Met Asp Glu Ala His Glu
```

-continued

```
                645                 650                 655
Arg Ser Leu Asn Thr Asp Val Leu Phe Gly Leu Leu Arg Glu Val Val
                660                 665                 670
Ala Arg Arg Ser Asp Leu Lys Leu Ile Val Thr Ser Ala Thr Met Asp
        675                 680                 685
Ala Glu Lys Phe Ala Ala Phe Phe Gly Asn Val Pro Ile Phe His Ile
    690                 695                 700
Pro Gly Arg Thr Phe Pro Val Asp Ile Leu Phe Ser Lys Thr Pro Gln
705                 710                 715                 720
Glu Asp Tyr Val Glu Ala Val Lys Gln Ser Leu Gln Val His Leu
                725                 730                 735
Ser Gly Ala Pro Gly Asp Ile Leu Ile Phe Met Pro Gly Gln Glu Asp
            740                 745                 750
Ile Glu Val Thr Ser Asp Gln Ile Val Glu His Leu Glu Glu Leu Glu
                755                 760                 765
Asn Ala Pro Ala Leu Ala Val Leu Pro Ile Tyr Ser Gln Leu Pro Ser
770                 775                 780
Asp Leu Gln Ala Lys Ile Phe Gln Lys Ala Pro Asp Gly Val Arg Lys
785                 790                 795                 800
Cys Ile Val Ala Thr Asn Ile Ala Glu Thr Ser Leu Thr Asp Gly Ile
                805                 810                 815
Met Phe Val Ile Asp Ser Gly Tyr Cys Lys Leu Lys Val Phe Asn Pro
            820                 825                 830
Arg Ile Gly Met Asp Ala Leu Gln Ile Tyr Pro Ile Ser Gln Ala Asn
                835                 840                 845
Ala Asn Gln Arg Ser Gly Arg Ala Gly Arg Thr Gly Pro Gly Gln Cys
    850                 855                 860
Phe Arg Leu Tyr Thr Gln Ser Ala Tyr Lys Asn Glu Leu Leu Thr Thr
865                 870                 875                 880
Thr Val Pro Glu Ile Gln Arg Thr Asn Leu Ala Asn Val Val Leu Leu
            885                 890                 895
Leu Lys Ser Leu Gly Val Gln Asp Leu Leu Gln Phe His Phe Met Asp
                900                 905                 910
Pro Pro Pro Glu Asp Asn Met Leu Asn Ser Met Tyr Gln Leu Trp Ile
        915                 920                 925
Leu Gly Ala Leu Asp Asn Thr Gly Gly Leu Thr Ser Thr Gly Arg Leu
    930                 935                 940
Met Val Glu Phe Pro Leu Asp Pro Ala Leu Ser Lys Met Leu Ile Val
945                 950                 955                 960
Ser Cys Asp Met Gly Cys Ser Ser Glu Ile Leu Leu Ile Val Ser Met
                965                 970                 975
Leu Ser Val Pro Ala Ile Phe Tyr Arg Pro Lys Gly Arg Glu Glu Glu
            980                 985                 990
Ser Asp Gln Ile Arg Glu Lys Phe Ala Val Pro Glu Ser Asp His Leu
        995                 1000                1005
Thr Tyr Leu Asn Val Tyr Leu Gln Trp Lys Asn Asn Tyr Ser Thr
    1010                1015                1020
Ile Trp Cys Asn Asp His Phe Ile His Ala Lys Ala Met Arg Lys Val
1025                1030                1035                1040
Arg Glu Val Arg Ala Gln Leu Lys Asp Ile Met Val Gln Gln Arg Met
            1045                1050                1055
Ser Leu Ala Ser Cys Gly Thr Asp Trp Asp Ile Val Arg Lys Cys Ile
    1060                1065                1070
```

-continued

Cys Ala Ala Tyr Phe His Gln Ala Ala Lys Leu Lys Gly Ile Gly Glu
        1075                1080                1085

Tyr Val Asn Ile Arg Thr Gly Met Pro Cys His Leu His Pro Thr Ser
    1090                1095                1100

Ser Leu Phe Gly Met Gly Tyr Thr Pro Asp Tyr Ile Val Tyr His Glu
1105                1110                1115                1120

Leu Val Met Thr Thr Lys Glu Tyr Met Gln Cys Val Thr Ala Val Asp
            1125                1130                1135

Gly Glu Trp Leu Ala Glu Leu Gly Pro Met Phe Tyr Ser Val Lys Gln
        1140                1145                1150

Ala Gly Lys Ser Arg Gln Glu Asn Arg Arg Ala Lys Glu Glu Ala
        1155                1160                1165

Ser Ala Met Glu Glu Glu Met Ala Leu Ala Glu Gln Leu Arg Ala
    1170                1175                1180

Arg Arg Gln Glu Gln Glu Lys Arg Ser Pro Leu Gly Ser Val Arg Ser
1185                1190                1195                1200

Thr Lys Ile Tyr Thr Pro Gly Arg Lys Glu Gln Gly Glu Pro Met Thr
            1205                1210                1215

Pro Arg Arg Thr Pro Ala Arg Phe Gly Leu
        1220                1225

<210> SEQ ID NO 8
<211> LENGTH: 3678
<212> TYPE: DNA
<213> ORGANISM: Homo sapiens

<400> SEQUENCE: 8
ggggacacca gtgaggatgc ctcgatccat cgattggaag gcactgatct ggactgtcag     60
gttggtggtc ttatttgcaa gtccaaaagt gcggccagcg cagcatgtct tcaaggctcc    120
tgctccccgc ccttcattac tcggactgga ttgctggctt ccctgaaacg agagagcga    180 gaggagaagg acgatgggga ggacaagaag aagtccaaag tctcctccta caaggactgg    240
gaagagagca aggatgacca aaggatgct gaggaagagg cgtgacca ggctggccaa     300 aatatccgaa agacagaca ttatcggtct gctcgggtag agactccatc ccatccgggt    360
ggtgtgagcg aagagttttg ggaacgcagt cggcagagag agcgggagcg gcgggaacat    420
ggtgtctatg cctcgtccaa agaagaaag gattggaaga aggagaaatc gcgggatcga    480
gactatgacc gcaagaggga cagagatgag cgggatagaa gtaggcacag cagcagatca    540
gagcgagatg gagggtcaga gcgtagcagc agaagaaatg aacccgagag cccacgacat    600
cgacctaaag atgcagccac cccttcaagg tctacctggg aggaagagga cagtggctat    660
ggctcctcaa ggcgctcaca gtgggaatcg ccctccccga cgccttccta tcgggattct    720
gagcggagcc atcggctgtc cactcgagat cgagacaggt ctgtgagggg caagtactcg    780
gatgacacgc ctctgccaac tccctcctac aaatataacg agtgggccga tgacagaaga    840
cacttggggt ccaccccgcg tctgtccagg ggccgaggaa gacgtgagga gggcgaagaa    900
ggaatttcat tgacacgga ggaggagcgg cagcagtggg aagatgacca gaggcaagcc    960
gatcgggatt ggtacatgat ggacgagggc tatgacgagt tccacaaccc gctgccctac   1020
tcctccgagg actacgtgag gaggcgggag cagcacctgc ataaacagaa gcagaagcgc   1080
atttcagctc agcggagaca gatcaatgag gataacgagc gctgggagac aaaccgcatg   1140
ctcaccagtg gggtggtcca tcggctggag gtggatgagg actttgaaga ggacaacgcg   1200

-continued

```
gccaaggtgc atctgatggt gcacaatctg gtgcctccct ttctggatgg gcgcattgtc   1260
ttcaccaagc agccggagcc ggtgattcca gtgaaggatg ctacttctga cctggccatc   1320
attgctcgga aaggcagcca gacagtgcgg aagcacaggg agcagaagga gcgcaagaag   1380
gctcagcaca aacactggga actggcgggg accaaactgg gagatataat gggcgtcaag   1440
aaggaggaag agccagataa agctgtgacg gaggatggga aggtggacta caggacagag   1500
cagaagtttg cagatcacat gaagagaaag agcgaagcca gcagtgaatt tgcaaagaag   1560
aagtccatcc tggagcagag gcagtacctg cccatctttg cagtgcagca ggagctgctc   1620
actattatca gagacaacag catcgtgatc gtggttgggg agacggggag tggtaagacc   1680
actcagctga cgcagtacct gcatgaagat ggttacacgg actatgggat gattgggtgt   1740
acccagcccc ggcgtgtagc tgccatgtca gtggccaaga gagtcagtga agagatgggg   1800
ggaaaccttg gcgaggaggt gggctatgcc atccgctttg aagactgcac ttcagagaac   1860
accttgatca aatacatgac tgacgggatc ctgctccgag agtccctccg ggaagccgac   1920
ctggatcact acagtgccat catcatggac gaggcccacg agcgctccct caacactgac   1980
gtgctctttg ggctgctccg ggaggtagtg gctcggcgct cagacctgaa gctcatcgtc   2040
acatcagcca cgatggatgc ggagaagttt gctgcctttt ttgggaatgt ccccatcttc   2100
cacatccctg gccgtaccct ccctgttgac atcctcttca gcaagacccc acaggaggat   2160 tacgtgagg ctgcagtgaa gcagtccttg caggtgcacc tgtcgggggc ccctggagac   2220
atccttatct tcatgcctgg ccaagaggac attgaggtga cctcagacca gattgtggag   2280
catctggagg aactggagaa cgcgcctgcc ctggctgtgc tgcccatcta ctctcagctg   2340
ccttctgacc tccaggccaa atcttccag aaggctccag atggcgttcg gaagtgcatc   2400
gttgccacca atattgccga cgtctctc actgttgacg gcatcatgtt tgttatcgat   2460
tctggttatt gcaaattaaa ggtcttcaac cccaggattg gcatggatgc tctgcagatc   2520
tatcccatta gccaggccaa tgccaaccag cggtcagggc gagccggcag gacgggccca   2580
ggtcagtgtt tcaggctcta cacccagagc gcctacaaga atgagctcct gaccaccaca   2640
gtgcccgaga tccagaggac taacctggcc aacgtggtgc tgctgctcaa gtccctcggg   2700
gtgcaggacc tgctgcagtt ccacttcatg acccgcccc cggaggacaa catgctcaac   2760
tctatgtatc agctctggat cctcgggccc ctggacaaca caggtggtct gacctctacc   2820
gggcggctga tggtggagtt cccgctggac cctgccctgt ccaagatgct catcgtgtcc   2880
tgtgacatgg gctgcagctc cgagatcctg ctcatcgttt ccatgctctc ggtcccagcc   2940
atcttctaca ggcccaaggg tcgagaggag gagagtgatc aaatccggga gaagttcgct   3000
gttcctgaga gcgatcattt gacctacctg aatgtttacc tgcagtggaa gaacaataat   3060
tactccacca tctggtgtaa cgatcatttc atccatgcta aggccatgcg gaaggtccgg   3120
gaggtgcgag ctcaactcaa ggacatcatg gtgcagcagc ggatgagcct ggcctcgtgt   3180
ggcactgact gggacatcgt caggaagtgc atctgtgctg cctatttcca ccaagcagcc   3240
aagctcaagg gaatcgggga gtacgtgaac atccgcacag ggatgccctg ccacttgcac   3300
cccaccagct cccttttgg aatgggctac accccagatt acatagtgta tcacgagttg   3360
gtcatgacca ccaaggagta tatgcagtgt gtgaccgctg tggacgggga gtggctggcg   3420
gagctgggcc ccatgttcta tagcgtgaaa caggcgggca agtcacggca ggagaaccgt   3480
cgtcgggcca aagaggaagc ctctgccatg gaggaggaga tggcgctggc cgaggagcag   3540
ctgcgagccc ggcggcagga gcaggagaag cgcagccccc tggcagtgt caggtctacg   3600
```

-continued

| | |
|---|---|
| aagatctaca ctccaggccg aaagagcaa ggggagccca tgacccctcg ccgcacgcca | 3660 |
| gcccgctttg gtctgtga | 3678 |

<210> SEQ ID NO 9
<211> LENGTH: 4121
<212> TYPE: DNA
<213> ORGANISM: Homo sapiens

<400> SEQUENCE: 9

| | |
|---|---|
| ggggacacca gtgaggatgc ctcgatccat cgattggaag gcactgatct ggactgtcag | 60 |
| gttggtggtc ttatttgcaa gtccaaaagt gcggccagcg agcagcatgt cttcaaggct | 120 |
| cctgctcccc gccctttcatt actcggactg gacttgctgg cttccctgaa acggagagag | 180 |
| cgagaggaga aggacgatgg ggaggacaag aagaagtcca agtctcctc ctacaaggac | 240 |
| tgggaagaga gcaaggatga ccagaaggat gctgaggaag agggcggtga ccaggctggc | 300 |
| caaaatatcc ggaaagacag acattatcgg tctgctcggg tagagactcc atcccatccg | 360 |
| ggtggtgtga gcgaagagtt ttgggaacgc agtcggcaga gagagcggga gcggcgggaa | 420 |
| catggtgtct atgcctcgtc caaagaagaa aaggattgga agaaggagaa atcgcgggat | 480 |
| cgagactatg accgcaagag ggacagagat gagcgggata gaagtaggca cagcagcaga | 540 |
| tcagagcgag atggagggtc agagcgtagc agcagaagaa atgaacccga gccccacga | 600 |
| catcgaccta agatgcagc caccccttca aggtctacct gggaggaaga ggacagtggc | 660 |
| tatggctcct caaggcgctc acagtgggaa tcgccctccc cgacgccttc ctatcgggat | 720 |
| tctgagcgga gccatcggct gtccactcga gatcgagaca ggtctgtgag gggcaagtac | 780 |
| tcggatgaca cgcctctgcc actccctcct acaaatataa cgagtgggcc gatgacagaa | 840 |
| gacacttggg gtccaccccg cgtctgtcca ggggccgagg aagacgtgag gagggcgaag | 900 |
| aaggaatttc atttgacacg gaggaggagc ggcagcagtg ggaagatgac cagaggcaag | 960 |
| ccgatcggga ttggtacatg atggacgagg gctatgacga gttccacaac ccgctggcct | 1020 |
| actcctccga ggactacgtg aggaggcggg agcagcacct gcataaacag aagcagaagc | 1080 |
| gcatttcagc tcagcggaga cagatcaatg aggataacga gcgctgggag acaaaccgca | 1140 |
| tgctcaccag tggggtggtc catcggctgg aggtggatga ggactttgaa gaggacaacg | 1200 |
| cggccaaggt gcatctgatg gtgcacaatc tggtgcctcc ctttctggat gggcgcattg | 1260 |
| tcttccacaa gcagccggag ccggtgattc cagtgaagga tgctacttct gacctggcca | 1320 |
| tcattgctcg gaaaggcagc cagacagtgc ggaagcacag ggagcagaag gagcgcaaga | 1380 |
| aggctcagca caaacactgg gaactggcgg ggaccaaact gggagatata atgggcgtca | 1440 |
| agaaggagga agagccagat aaagctgtga cggaggatgg gaaggtggac tacaggacag | 1500 |
| agcagaagtt tgcagatcac atgaagagaa agagcgaagc cagcagtgaa tttgcaaaga | 1560 |
| agaagtccat cctggagcag aggcagtacc tgcccatctt tgcagtgcag caggagctgc | 1620 |
| tcactattat cagagacaac agcatcgtga tcgtggttgg ggagacgggg agtggtaaga | 1680 |
| ccactcagct gacgcagtac ctgcatgaag atggttacac ggactatggg atgattgggt | 1740 |
| gtacccagcc ccgcgtgta gctgccatgt cagtggccaa gagagtcagt gaagagatgg | 1800 |
| ggggaaacct tggcgaggag gtgggctatg ccatccgctt tgaagactgc acttcagaga | 1860 |
| acaccttgat caaatacatg actgacggga tcctgctccg agagtccctc cgggaagccg | 1920 |
| acctggatca ctacagtgcc atcatcatgg acgaggccca cgagcgctcc ctcaacactg | 1980 |

```
acgtgctctt tgggctgctc cgggaggtag tggctcggcg ctcagacctg aagctcatcg    2040
tcacatcagc cacgatggat gcggagaagt ttgctgcctt ttttgggaat gtccccatct    2100
tccacatccc tggccgtacc ttccctgttg acatcctctt cagcaagacc ccacaggagg    2160
attacgtgga ggctgcagtg aagcagtcct tgcaggtgca cctgtcgggg gcccctggag    2220
acatccttat cttcatgcct ggccaagagg acattgaggt gacctcagac cagattgtgg    2280
agcatctgga ggaactggag aacgcgcctg ccctggctgt gctgcccatc tactctcagc    2340
tgccttctga cctccaggcc aaaatcttcc agaaggctcc agatggcgtt cggaagtgca    2400
tcgttgccac caatattgcc gagacgtctc tcactgttga cggcatcatg tttgttatcg    2460
attctggtta ttgcaaatta aaggtcttca accccaggat tggcatggat gctctgcaga    2520
tctatcccat tagccaggcc aatgccaacc agcggtcagg gcgagccggc aggacgggcc    2580
caggtcagtg tttcaggctc tacacccaga gcgcctacaa gaatgagctc ctgaccacca    2640
cagtgcccga gatccagagg actaacctgg ccaacgtggt gctgctgctc aagtccctcg    2700
gggtgcagga cctgctgcag ttccacttca tggacccgcc cccggaggac aacatgctca    2760
actctatgta tcagctctgg atcctcgggg ccctggacaa cacaggtggt ctgacctcta    2820
ccgggcggct gatggtggag ttcccgctgg accctgccct gtccaagatg ctcatcgtgt    2880
cctgtgacat gggctgcagc tccgagatcc tgctcatcgt ttccatgctc tcggtcccag    2940
ccatcttcta caggcccaag ggtcgagagg aggagagtga tcaaatccgg gagaagttcg    3000
ctgttcctga gagcgatcat ttgacctacc tgaatgttta cctgcagtgg aagaacaata    3060
attactccac catctggtgt aacgatcatt tcatccatgc taaggccatg cggaaggtcc    3120
gggaggtgcg agctcaactc aaggacatca tggtgcagca gcggatgagc ctggcctcgt    3180
gtggcactga ctgggacatc gtcaggaagt gcatctgtgc tgcctatttc caccaagcag    3240
ccaagctcaa gggaatcggg gagtacgtga acatccgcac agggatgccc tgccacttgc    3300
accccaccag ctcccttttt ggaatgggct acaccccaga ttacatagtg tatcacgagt    3360
tggtcatgac caccaaggag tatatgcagt gtgtgaccgc tgtggacggg gagtggctgg    3420
cggagctggg ccccatgttc tatagcgtga acaggcgggg caagtcacgg caggagaacc    3480
gtcgtcgggc caaagaggaa gcctctgcca tggaggagga gatggcgctg ccgaggagc    3540 agctgcgagc ccggcggcag gagcaggaga gcgcagccc cctgggcagt gtcaggtcta    3600
cgaagatcta cactccaggc cggaaagagc aaggggagcc catgacccct cgccgcacgc    3660
cagcccgctt tggtctgtga gctgaggctg tccccagaga ggatggcagc agggcagttc    3720
ctgctggacc agactctctg gcagaggagg tggagttctt ccatgcagga gcacggcatg    3780
gcgggagcgg ggctgcagag tatccgaggt gctgccgggg cagcgggagg tggctggacc    3840
catcgcatct aaaactggcc caggacactt ggtgtatgcg tgacttggct gtggctgtct    3900
tttttaatcc ttgtgtaaag cagcaaaaaa gacctaaagg gaattgtaat ttggttataa    3960
ttcaggattt ggaaataaat ttattatttg taaaacaaaa aaaaaatct ccaaaaaaaa     4020 aaaaaaaaaa aaaaaaaaa aaaaaaaaa aaaaaaaaa aaaaaaaaa aaaaaaaaaa       4080 aaaaaaaaaa aaaaaaaaa aaaaaaaaa aaaaaaaaa a                           4121
```

<210> SEQ ID NO 10
<211> LENGTH: 441
<212> TYPE: DNA
<213> ORGANISM: Artificial Sequence
<220> FEATURE:
<223> OTHER INFORMATION: p153-NT3

<400> SEQUENCE: 10

```
gctgaggctg tccccagaga ggatggcagc agggcagttc ctgctggacc agactctctg      60
gcagaggagg tggagttctt ccatgcagga gcacggcatg gcgggagcgg ggctgcagag     120
tatccgaggt gctgccgggg cagcgggagg tggctggacc catcgcatct aaaactggcc     180
caggacactt ggtgtatgcg tgacttggct gtggctgtct tttttaatcc ttgtgtaaag     240
cagcaaaaaa gacctaaagg gaattgtaat ttggttataa ttcaggattt ggaaataaat     300
ttattatttg taaaacaaaa aaaaaatct ccaaaaaaaa aaaaaaaaaa aaaaaaaaa       360
aaaaaaaaaa aaaaaaaaaa aaaaaaaaaa aaaaaaaaaa aaaaaaaaaa aaaaaaaaaa     420
aaaaaaaaaa aaaaaaaaaa a                                               441
```

<210> SEQ ID NO 11
<211> LENGTH: 72
<212> TYPE: DNA
<213> ORGANISM: Artificial Sequence
<220> FEATURE:
<223> OTHER INFORMATION: p153-Pi3

<400> SEQUENCE: 11

```
cagctttcta gaacaaaaat catctcagaa gaggatctga atagcgccgt cgaccatcat      60
catcatcatc at                                                         72
```

<210> SEQ ID NO 12
<211> LENGTH: 42
<212> TYPE: DNA
<213> ORGANISM: Artificial Sequence
<220> FEATURE:
<223> OTHER INFORMATION: p135-NT5C

<400> SEQUENCE: 12

```
atgtccccta tagatccgat gggacatcat catcatcatc ac                        42
```

<210> SEQ ID NO 13
<211> LENGTH: 72
<212> TYPE: DNA
<213> ORGANISM: Artificial Sequence
<220> FEATURE:
<223> OTHER INFORMATION: p135-NT5s

<400> SEQUENCE: 13

```
atggccctgt ggatgcgcct cctgcccctg ctggcgctgc tggccctctg gggacctgac      60
ccggcccaag cc                                                         72
```

<210> SEQ ID NO 14
<211> LENGTH: 267
<212> TYPE: DNA
<213> ORGANISM: Artificial Sequence
<220> FEATURE:
<223> OTHER INFORMATION: p135-NTPS

<400> SEQUENCE: 14

```
atgagatttc cttcaatttt tactgctgtt ttattcgcag catcctccgc attagctgct      60
ccagtcaaca ctacaacaga agatgaaacg gcacaaattc cggctgaagc tgtcatcggt     120
tactcagatt tagaagggga tttcgatgtt gctgttttgc cattttccaa cagcacaaat     180
aacgggttat tgtttataaa tactactatt gccagcattg ctgctaaaga agaagggta      240
tctctcgaga aaagagaggc tgaagct                                         267
```

```
<210> SEQ ID NO 15
<211> LENGTH: 12
<212> TYPE: DNA
<213> ORGANISM: Artificial Sequence
<220> FEATURE:
<223> OTHER INFORMATION: p135-NTGEX

<400> SEQUENCE: 15
ctggttccgc gt                                                          12

<210> SEQ ID NO 16
<211> LENGTH: 195
<212> TYPE: DNA
<213> ORGANISM: Artificial Sequence
<220> FEATURE:
<223> OTHER INFORMATION: Baculovirus transfer vector

<400> SEQUENCE: 16 atgtcccta tagatccgat gggacatcat catcatcatc acggaaggag aagggccagt        60
gttgcggcgg gaattttggt ccctcgtgga agcccaggac tcgatggcat atgctcgatc      120
gaggaattca ggcctccatg ggagctcgcg gccgcctgca gggtaccccc gggagatctg      180
taccgactct gctga                                                      195

<210> SEQ ID NO 17
<211> LENGTH: 64
<212> TYPE: PRT
<213> ORGANISM: Artificial Sequence
<220> FEATURE:
<223> OTHER INFORMATION: Baculovirus transfer vector fusion protein

<400> SEQUENCE: 17

Met Ser Pro Ile Asp Pro Met Gly His His His His His His Gly Arg
 1               5                  10                  15

Arg Arg Ala Ser Val Ala Ala Gly Ile Leu Val Pro Arg Gly Ser Pro
                20                  25                  30

Gly Leu Asp Gly Ile Cys Ser Ile Glu Glu Phe Arg Pro Pro Trp Glu
            35                  40                  45

Leu Ala Ala Ala Cys Arg Val Pro Pro Gly Asp Leu Tyr Arg Leu Cys
        50                  55                  60

<210> SEQ ID NO 18
<211> LENGTH: 111
<212> TYPE: DNA
<213> ORGANISM: Artificial Sequence
<220> FEATURE:
<223> OTHER INFORMATION: Baculovirus transfer vector

<400> SEQUENCE: 18
ggatcccggt ccgaagcgcg cggaattcaa aggcctacgt cgacgagctc actagtcgcg        60
gccgctttcg aatctagagc ctgcagtctc gaggcatgcg gtaccaagct t                111

<210> SEQ ID NO 19
<211> LENGTH: 6
<212> TYPE: DNA
<213> ORGANISM: Artificial Sequence
<220> FEATURE:
<223> OTHER INFORMATION: Binding Site

<400> SEQUENCE: 19 aataaa                                                                   6

<210> SEQ ID NO 20
```

```
<211> LENGTH: 6
<212> TYPE: DNA
<213> ORGANISM: Artificial Sequence
<220> FEATURE:
<223> OTHER INFORMATION: Binding Site

<400> SEQUENCE: 20 attaaa                                                              6

<210> SEQ ID NO 21
<211> LENGTH: 8
<212> TYPE: DNA
<213> ORGANISM: Artificial Sequence
<220> FEATURE:
<223> OTHER INFORMATION: GT-rich element

<400> SEQUENCE: 21 ygtgttyy                                                            8

<210> SEQ ID NO 22
<211> LENGTH: 43
<212> TYPE: PRT
<213> ORGANISM: Homo sapiens
<220> FEATURE:
<221> NAME/KEY: VARIANT
<222> LOCATION: 2, 3, 4, 28, 29, 30, 34, 41, 42
<223> OTHER INFORMATION: Xaa = Any Amino Acid

<400> SEQUENCE: 22

Ala Xaa Xaa Xaa Gly Lys Thr Pro Thr Arg Glu Leu Ala Gly Gly Thr
 1               5                  10                  15

Pro Gly Arg Asp Glu Ala Asp Ser Ala Thr Phe Xaa Xaa Xaa Thr Arg
            20                  25                  30

Gly Xaa Asp His Arg Ile Gly Arg Xaa Xaa Arg
         35                  40

<210> SEQ ID NO 23
<211> LENGTH: 43
<212> TYPE: PRT
<213> ORGANISM: Homo sapiens
<220> FEATURE:
<221> NAME/KEY: VARIANT
<222> LOCATION: 2, 3, 4, 5, 45, 46
<223> OTHER INFORMATION: Xaa = Any Amino Acid

<400> SEQUENCE: 23

Ala Xaa Xaa Xaa Xaa Gly Lys Thr Pro Thr Arg Glu Leu Ala Gly Gly
 1               5                  10                  15

Thr Pro Gly Arg Asp Glu Ala Asp Ser Ala Thr Phe Ile Asn Thr Arg
            20                  25                  30

Gly Ile Asp His Arg Ile Gly Arg Xaa Xaa Arg
         35                  40

<210> SEQ ID NO 24
<211> LENGTH: 40
<212> TYPE: PRT
<213> ORGANISM: Homo sapiens
<220> FEATURE:
<221> NAME/KEY: VARIANT
<222> LOCATION: 2, 3, 4, 5, 13, 14, 18, 27, 29, 31, 32, 38
<223> OTHER INFORMATION: Xaa = Any Amino Acid

<400> SEQUENCE: 24

Gly Xaa Xaa Xaa Xaa Gly Lys Thr Arg Val Ala Ala Xaa Xaa Thr Asp
 1               5                  10                  15
```

```
Gly Xaa Asp Glu Ala His Ser Ala Thr Phe Xaa Thr Xaa Gly Xaa Xaa
            20                  25                  30

Gln Arg Ile Gly Arg Xaa Gly Arg
        35                  40
```

<210> SEQ ID NO 25
<211> LENGTH: 37
<212> TYPE: PRT
<213> ORGANISM: Homo sapiens
<220> FEATURE:
<221> NAME/KEY: VARIANT
<222> LOCATION: 1, 2, 3, 4, 5, 12, 13, 14, 17, 23, 24, 26, 28, 29, 32,
      35
<223> OTHER INFORMATION: Xaa = Any Amino Acid

<400> SEQUENCE: 25

```
Xaa Xaa Xaa Xaa Xaa Gly Lys Thr Pro Thr Arg Xaa Xaa Xaa Asp Glu
1               5                   10                  15

Xaa His Thr Ala Thr Phe Xaa Xaa Ser Xaa Gly Xaa Xaa Gln Arg Xaa
            20                  25                  30

Gly Arg Xaa Gly Arg
        35
```

<210> SEQ ID NO 26
<211> LENGTH: 32
<212> TYPE: PRT
<213> ORGANISM: Homo sapiens

<400> SEQUENCE: 26

```
Gly Gly Lys Thr Pro Thr Arg Glu Leu Ala Cys Gly Thr Pro Gly Arg
1               5                   10                  15

Asp Glu Ala Asp Ser Ala Thr Arg Gly Asp Lys Arg Ile Gly Arg Arg
            20                  25                  30
```

<210> SEQ ID NO 27
<211> LENGTH: 20
<212> TYPE: PRT
<213> ORGANISM: Homo sapiens

<400> SEQUENCE: 27

```
Gly Gly Lys Thr Pro Arg Ala Thr Gly Asp Glu Ala Arg Ser Ala Thr
1               5                   10                  15

Arg Gly Arg Arg
        20
```

<210> SEQ ID NO 28
<211> LENGTH: 18
<212> TYPE: PRT
<213> ORGANISM: Homo sapiens

<400> SEQUENCE: 28

```
Gly Gly Lys Pro Arg Ala Thr Gly Asp Glu Trp Ser Ala Thr Arg Gly
1               5                   10                  15

Arg Arg
```

<210> SEQ ID NO 29
<211> LENGTH: 11
<212> TYPE: PRT
<213> ORGANISM: Homo sapiens

<400> SEQUENCE: 29

```
Gly Gly Lys Thr Asp Glu Ala His Ala Gly Arg
1               5                   10
```

EXPRESSION VECTOR FOR THE PRODUCTION OF DEAD PROTEINS

The present invention relates to an insect cell vector for the production of proteins from the DEAD protein family.

The modulation of the RNA structure plays an essential role in cellular processes, such as, for example, in pre-mRNA splicing, in RNA transport or in protein translation, as the cellular RNA is present in the cell in different secondary and tertiary structures and, in addition, a large number of RNA-binding proteins provides for further structuring of the RNA. Proteins from the family of the so-called DEAD box proteins, inter alia, are involved in these modulation processes. The members of this protein superfamily, which as a characteristic contain a number of homologous protein sequences, so-called "protein boxes", are named after the highly conserved tetrapeptide Asp-Glu-Ala-Asp (residues 21–24 of SEQ ID NO: 23) in the single-letter code D-E-A-D, as a motif. This protein superfamily also includes a number of RNA and DNA helicases.

The characteristic protein sequences of the DEAD proteins are highly conserved in evolution. A schematic representation of the proteins from the DEAD superfamily and its subfamilies as in FIG. 1 shows the similarity between the individual family members (see also Schmid, S. R. & Linder, P. (1992) Molecular Microbiology, 6, 283, No. 3; Fuller-Pace F. V. (1994) Trends in Cell Biology, 4, 271). It is recognized that the DEAD superfamily is divided into various subfamilies, which according to their sequence motif are called DEAH, DEXH or DEAH* subfamily. All family members have an ATP-binding and RNA-binding function and also an ATP hydrolysis and RNA helicase function.

EP-A-0778347 now describes a novel ATP- and nucleic acid-binding protein having putative helicase and ATPase properties, which is assigned to the DEAH subfamily. In addition to the properties mentioned, the RNA helicase described is also connected with the tolerance of certain cells to leflunomide and related compounds and is thus suitable for the production of cell lines which are helpful in cancer, inflammation and apoptosis research and also in the elucidation of mechanisms of action of pharmaceuticals. A further possibility of application of this helicase is the identification of already known substances with respect to possible pharmaceutical properties such as, for example, an anticarcinogenic or antiviral action in a test or assay system. Sufficient amounts of the protein, however, are necessary for the desired types of use of the RNA helicase.

Interestingly, it has not been possible to date to homologously or heterologously express proteins from the DEAD protein superfamily in adequate amounts functionally. In addition to the size of the proteins, many representatives of this family have a molecular mass of 100 kD and above, certain structural motifs appear to inhibit the expression in foreign organisms. In particular, it is suspected of the so-called RS domain, a region of between 50 and 200 amino acids in size, which exhibits a greatly increased number of argenine-serine repetitions (single-letter code RS), that it directly or indirectly complicates protein expression. A direct effect can be caused, for example, by incorrect phosphorylation of the serine residues in this region. Indirectly, overexpression of proteins with this domain can cause toxic effects in the cell, as specific protein-protein interactions are mediated via this protein domain. In the case of heterologous protein overexpression, the native interaction can thus be disturbed or inhibited via RS domains.

The family of RS proteins is a "subfamily" of proteins which is defined by the possession of the RS domain. These proteins are involved in the most different of processes of pre-mRNA splicing. RS domains can mediate protein-protein interactions, influence RNA binding, modulate RNA-RNA annealing and function as subcellular location signals. The relationship between the DEAD box and the RS proteins consists in the fact that both are involved in the modulation of RNA structure and function and therefore many proteins are to be assigned to the protein families.

The RS domain in human RNA helicase according to SEQ ID No. 7 is in the range from about 131 to about 253 and in particular in the range from about 175 to about 216 based on the amino acid position.

It was therefore the object of the present invention to make available a process which makes possible the production by genetic engineering of proteins from the DEAD protein superfamily in large amounts.

It has now surprisingly been found that, in contrast to expression in E. coli or yeast, expression in insect cells is possible in an advantageous manner.

One subject of the present invention is therefore an insect cell vector comprising a nucleic acid coding for a protein from the DEAD protein superfamily. The term "nucleic acid" is understood according to the present invention as meaning preferably single- or double-stranded DNA or RNA, in particular double-stranded DNA.

In a preferred embodiment, the coding nucleic acid at the 3' end of the coding region additionally contains a native 3'-noncoding region, which in preferred embodiments is at least about 50, preferably about 50 to about 450, in particular about 50 to about 400, nucleotides long.

"Native" within the meaning of the present invention designates 3'-noncoding nucleic acid regions which originates from the same organism, preferably from the same gene as the coding nucleic acid. If, for example, the nucleic acid codes for a human RNA helicase according to EP-A-0778347, the 3'-noncoding region according to the preferred embodiment likewise originates from human cells, in particular from the gene coding for the designated RNA helicase. The 3'-noncoding region according to SEQ ID No. 10 is preferred.

It is known that the 3'-noncoding region of genes can bind various regulatory proteins or factors. Thus, for example, the so-called "Cleavage and Polyadenylation Specificity Factor" (CPSF) binds to the noncoding RNA sequence AAUAAA. The CPSF protein consists of a complex of subunits with molecular weights of 160, 100, 73 and 30 kD. A further RNA binding protein is the so-called "Cleavage Stimulation Factor" (CstF). This protein is a heterotrimer of three subunits of 77, 64 and 50 kD. In addition, there are further RNA binding proteins such as the so-called "Cleavage Factors" CF I and CF II and also a poly(A) polymerase. The poly(A) polymerase is a polypeptide with a molecular mass of 83 kD. The polymerase is involved both in the poly(A) tail synthesis and in its cleavage. The extension of the poly(A) tail is strongly stimulated by the so-called "poly(A) binding protein II" (PABII). Further information and literature references are found in Wahle, E. (1995) Biochemica at Biophysica Acta, 1261, 183. Thus in addition to the AAUAAA binding sequence, Wahle, E. (1995), for example, also describes further consensus motifs such as a GU-rich region having the proposed consensus sequence YGUGUUYY and U-rich elements (see also Proudfoot, N. (1991) Cell, 64, 671–674).

In a preferred embodiment, the present invention therefore relates to 3'-noncoding regions which contains a binding site for the CPSF protein, the CstF protein, the CF I protein, the CF II protein, the poly(A) polymerase and/or the poly(A)-binding protein II (PABII), such as, for example, an AATAAA binding site, ATTAAA binding site, a GT-rich element, in particular a YGTGTTYY element, and/or a T-rich element designated in the form of its cDNA form.

A protein from the DEAD protein superfamily is understood according to the present invention as meaning proteins which have conserved motifs, under which a conserved motif contains the amino acid sequence DEAD, DEAH or DEXH. The proteins preferably contain sequence motifs which are responsible for a nucleic acid-binding activity, a helicase activity and/or an ATPase activity. The proteins in particular contain an RNA helicase and ATPase activity. FIG. 1 and FIG. 2 shows examples of the conserved motifs for the DEAD protein superfamily and the DEAH, DEXH or DEAH* subfamilies.

Within the meaning of the present invention, the term "DEAD protein superfamily" thus includes all proteins which fall within a group according to FIG. 1 or 2. Examples of proteins of this type are described in Fuller-Pace, F. V. (1994), supra, and Schmid, S. R. and Linder, P. (1992), supra. Further preferred proteins are those which impart to cells tolerance to isoxazole derivatives, such as, for example, leflunomide, and compounds related in action, such as, for example, brequinar. Human proteins are particularly preferred, in particular those from Table 1 and the RNA helicase from EP-A-0778347. Within the meaning of the present invention, proteins with a molecular mass of about 100 to about 150 kD, in particular with a molecular mass of about 130 kD, and those with a so-called SR domain, i.e. a region of about 50 to 200 amino acids in size with an increased number of arginine-serine repetitions, are preferably suitable. Within the meaning of the present invention, a nucleic acid coding for the human RNA helicase p135 according to EP 0778347 with the amino acid sequence as in FIG. 3 is particularly suitable.

TABLE 1

Human helicase genes

| Gene (or protein) | GenBank accession number |
|---|---|
| DEXH box DNA helicase | |
| XPB; ERCC3 | M31899 |
| XPD; ERCC2 | X52221; L47234 |
| DDW11 (CHLR1) | U33833 |
| DDX12 (CHLR2) | U33834 |
| RECQL | L36140; D37984 |
| BLM | U39817 |
| WRN | L76937 |
| CSB; ERCC6 | L04791 |
| ATRX | U09820; U72936–U72938 |
| HRAD54 | X97795 |
| SNF2L1 (SMBP2) | P28370*; L24544 |
| SNF2L2 (HBRM) | X72889 |
| SNF2L3 (HIP 116; HTLF) | Z46606 |
| SNF2L4 (BRG-1) | U29175 |
| DEAD box RNA helicase | |
| DDX5 (p68) | X15729; X52104 |
| DDX6 (RCK; p54) | Z11685; D17532 |
| (p72) | U59321 |
| (BAT1) | Z37166 |
| (MRDB) | X98743 |
| DDX10 | U28042 |
| (Gu; RNA helicase II) | U41387 |
| DDX7 (NP52) | D26528 |
| EIF4A (eIF4A-1) | D30655 |
| (eIF4A-like) | P38919* |
| DDX1 (cl. 1042) | X70649 |

TABLE 1-continued

Human helicase genes

| Gene (or protein) | GenBank accession number |
|---|---|
| DEXH box RNA helicase | |
| DDX9 (RNA helicase A) | L13848; Y10658 |
| DDX8 (HRH1) | D50487 |
| SKIV2L (SKI2W; 170A) | Z48796 |
| KIAA0134 | D50924 |
| (Mi-2) | X86691 |

*Swiss Prot accession number (from Ellis, N.A. (1997), Current Opinion in Genetics & Development, 7, 354)

A further preferred example of a nucleic acid coding for a protein from the DEAH protein subfamily with a native 3'-noncoding region is the cDNA of the human RNA helicase from EP-A-0778347 as in FIG. 5 of the present invention. The 3'-noncoding region of the RNA helicase mentioned according to SEQ ID No. 10 is generally suitable within the meaning of the present invention as a native 3'-noncoding region of human proteins from the DEAD protein superfamily and in particular from the DEAH protein subfamily.

In a preferred embodiment, the vector according to the invention contains regulatory sequences which control the expression of the nucleic acid coding for a protein from the DEAD protein superfamily. All the regulatory sequences known to the person skilled in the art are suitable for this. A promoter of a "long terminal repeat" (LTR), in particular of a retroviral LTR or of an LTR of a transposable element according to, for example, U.S. Pat. No. 5,004,687 are particularly suitable. Regulatory sequences from insect viruses, preferably baculoviruses, in particular the promoter of the polyhedrin gene or of the 10K protein (see, for example, EP-B1-0127839) are particularly suitable. In a further preferred embodiment, the native ATG start codon of the nucleic acid coding for a protein from DEAD protein superfamily is replaced by a polyhedrin-ATG translation initiation start site. The nucleic acid according to the present invention is thus a chimeric nucleic acid from insect virus sequences at the 5' end and heterologous sequences following downstream, the 3'-noncoding part preferably containing sequences native to the heterologous part. This construct according to the invention makes possible a further advantageous increase in expression in insect cells.

In another preferred embodiment, the nucleic acid according to the invention contains a nucleic acid coding for an oligopeptide of at least about 4, preferably of about 6, histidines between the ATG translation initiation start site and the region coding for the protein from the DEAD protein superfamily. After expression of the designated nucleic acid, a fusion protein is obtained from the chosen protein from the DEAD protein superfamily and an N-terminally fused peptide which contains the histidines mentioned. By this means, the protein can be purified in a particularly simple and effective manner, for example, by means of a metal ion-containing chromatography column, such as, for example, a nickel-containing chromatography column, such as Ni-NTA resin-containing chromatography column. "NTA" stands for the chelator "nitrilotriacetic acid" (Qiagen GmbH, Hilden). Instead of or in addition to the nucleic acid coding for the histidines mentioned, a nucleic acid can also be used which codes for the glutathione S-transferase (Smith, D. B. & Johnson, K. S. 1988) Gene, 67, 31–40). The fusion proteins thus obtained can likewise be purified in a simple manner by means of affinity chromatography and detected by means of a calorimetric test or by means of an immunoassay. A suitable system is, for example, the vector PGEX from Pharmacia, Freiburg as a starting vector.

For the removal of the foreign protein component from the fusion protein mentioned, it is advantageous if the nucleic acid codes for a protease cleavage site. Suitable proteases are, for example, thrombin, or factor Xa. The thrombin cleavage site contains for example, the amino acid sequence Leu-Val-Pro-Arg-Gly-Ser (SEQ ID NO: 1) (see, for example, FIG. 3B). The factor Xa cleavage site contains, for example, the amino acid sequence Ile-Glu-Gly-Arg (SEQ ID NO: 2).

A preferred 5' region of the nucleic acid according to the present invention is, for example, a nucleic acid according to FIG. 3B, which begins in the start codon ATG and ends after the thrombin cleavage site at one of the designated restriction enzyme cleavage sites. The nucleic acid concerned can then be ligated according to generally known processes at the selected restriction enzyme cleavage site. A suitable nucleic acid according to the invention is a nucleic acid comprising the polyhedrin promoter, e.g. according to EP-B1-0 127 839, the nucleic acid p135-NT5C according to SEQ ID No. 12 comprising the polyhedrin-ATG translation initiation start site and a sequence coding for 6 histidines and a nucleic acid according to SEQ ID No. 9 comprising a nucleic acid coding for the RNA helicase p135 and its native 3'-noncoding region.

In a further preferred embodiment, the 5' region of the nucleic acid according to the invention contains a nucleic acid which codes for a signal sequence, for example an insulin signal sequence, e.g. according to SEQ ID No. 13, in the form of the construct p135-NT5S. This construct also has the advantage that the desired protein can be worked up and purified particularly easily, as on account of the signal sequence it is secreted directly into the culture medium and in the course of this the signal sequence is removed, instead of accumulating the desired protein intracellularly in the insect cells. Further suitable signal sequences are the signal sequence of bombyxin of the silkworm (Congote, L. F. & Li, Q., (1994) Biochem. J., 299, 101–107), signal sequence of the human placental alkaline phosphatase (Mroczkowski, B. S. et al., (1994), J. Biol. Chem., 269, 13522–28), signal sequence of melittin from the honeybee (Mroczkowski, B. S. et al. (1994) J. Biol. Chem., 269, 13522–28; Chai, H. et al. (1993) Biotechnol. Appl. Biochem. (1993) 18, 259-73), signal sequence of the human plasminogen activator (Jarvis, D. L. & Summers, M. D. (1989) Mol. Cell. Biol., 9, 214–23), signal sequences of certain insect cell proteins (WO90/05783) or leader sequences of prokaryotic genes (EP-A1-0 486 170).

Another subject of the present invention is a process for the production of recombinant insect viruses which code for a protein from the DEAD protein superfamily according to the present invention, in which a vector according to the invention is introduced into insect cells together with insect virus wild-type DNA and the resulting recombinant insect viruses are isolated.

A suitable insect virus is, for example, the baculovirus, in particular the Autographa Californica virus. Suitable insect cells are, for example, Spodoptera Frugiperda, Trichoplusia ni, Rachiplusia ou or Galleria Mellonela. The Autographa Californica strains E2, R9, S1 or S3, especially the Autographa Californica strain S3, Spodoptera Frugiperda strain 21 or Trichoplusia ni egg cells are particularly suitable. In addition to the insect cells, ovarian cells of the corresponding insects or their larvae are also suitable. The recombinant insect virus according to the invention is formed in the insect cells by homologous recombination of the vector according to the invention with the insect virus wild type concerned (see, for example, EP-B1-0127839 or U.S. Pat. No. 5,004,687). The recombinant insect virus can then be used for the production of the desired protein.

A further subject of the present invention therefore also relates to a process for the production of a protein from the DEAD protein superfamily, in which a vector according to the invention or a recombinant insect virus according to the invention is introduced into insect cells or insect larvae, the insect cells or larvae are cultured under suitable conditions and the expressed protein is isolated. Preferably, insect cells are infected with recombinant insect virus, the infection period preferably being about 40 to about 90, in particular about 70, hours. The production of a recombinant insect virus or the production of a desired protein in insect cells is carried out by processes generally known to the person skilled in the art, such as are described, for example, in EP-B1-0127839 or U.S. Pat. No. 5,004,687. However, commercially obtainable baculovirus expression systems such as, for example, the Baculo Gold™ transfection kit from Pharmingen or the Bac-to-Bac™ baculovirus expression system from Gibco BRL are also suitable.

It is an advantage of the insect cell expression vectors according to the invention and the processes according to the invention that, surprisingly, relatively large amounts, in general about 300–400 mg per 10 cells, of proteins from the DEAD protein superfamily, in particular of proteins having a molecular mass of >about 100 kD and especially proteins having a so-called SR domain, can be produced.

A further subject of the present invention therefore relates to the use from an insect cell vector according to the invention for the production of a protein from the DEAD protein superfamily. The designated proteins are suitable, for example, for the production of appropriate test systems according to EP-A-0778347 or for the treatment of a disorder as described in EP-A-0778347 or in Ellis N. A. (1997), supra.

The following figures and examples are intended to illustrate the invention in greater detail without restricting it thereto.

DESCRIPTION OF THE FIGURES AND SEQUENCES

FIG. 1 (SEQ ID NOS: 22–25) schematically shows the conserved regions of the proteins from the DEAD protein superfamily and the DEAH and DEXH subfamilies, and, as an example, the conserved regions of the protein eIF-4A. The numbers between the regions indicate the distances in amino acids. X is any desired amino acid.

FIG. 2 schematically describes the conserved regions and their known functions of the proteins for the DEAD, DEAH, DEXH and DEAH* families (SEQ ID-NOS: 26–29), according to Fuller-Pace, F. V. (1994), supra.

SEQ ID No. 7 represents the amino acid sequence of the human RNA helicase p135. The RS domain is the position 131 to 253.

SEQ ID No. 8 represents the nucleic acid sequence of the human RNA helicase p135.

SEQ ID No. 9 represents the nucleic acid sequence of the human RNA helicase p135 including its 3'-noncoding region.

SEQ ID No. 10 is p135-NT3
SEQ ID No. 11 is p135-Pi3
SEQ ID No. 12 is p135-NT5C
SEQ ID No. 13 is p135-NT5S

SEQ ID No. 14 is p135-NTPS

SEQ ID No. 15 is p135-NTGEX.

FIGS. 3A and B schematically show the pAcHLT-A baculovirus transfer vector and coding sequences of the foreign portion in the fusion protein (Invitrogen®). 3B corresponds to SEQ ID No. 16 and SEQ ID No. 17.

FIGS. 4A and B schematically show the pFASTBAC1 baculovirus transfer vector and the cloning site (Gibco-BRL). 4B corresponds to SEQ ID No. 18.

FIG. 5 schematically shows the production of the vector KL33. p135-CDS denotes the coding p135-DNA sequence from the 2nd coding base triplet up to the last coding base triplet. p135-GS denotes the coding p135-DNA sequence from the 2nd coding base triplet up to the last base of the 3'-nontranslated region.

EXAMPLES

Example 1
Production of a Recombinant Baculovirus Expression Vector for the Cytosolic Expression of the p135 Protein All recombinant DNA methods were carried out by means of standard methods (see, for example, Sambrook, J. et al. (1989) Molecular Cloning. A Laboratory Manual 2nd ed. Cold Spring Harbor Laboratory Press).

Figure 5:
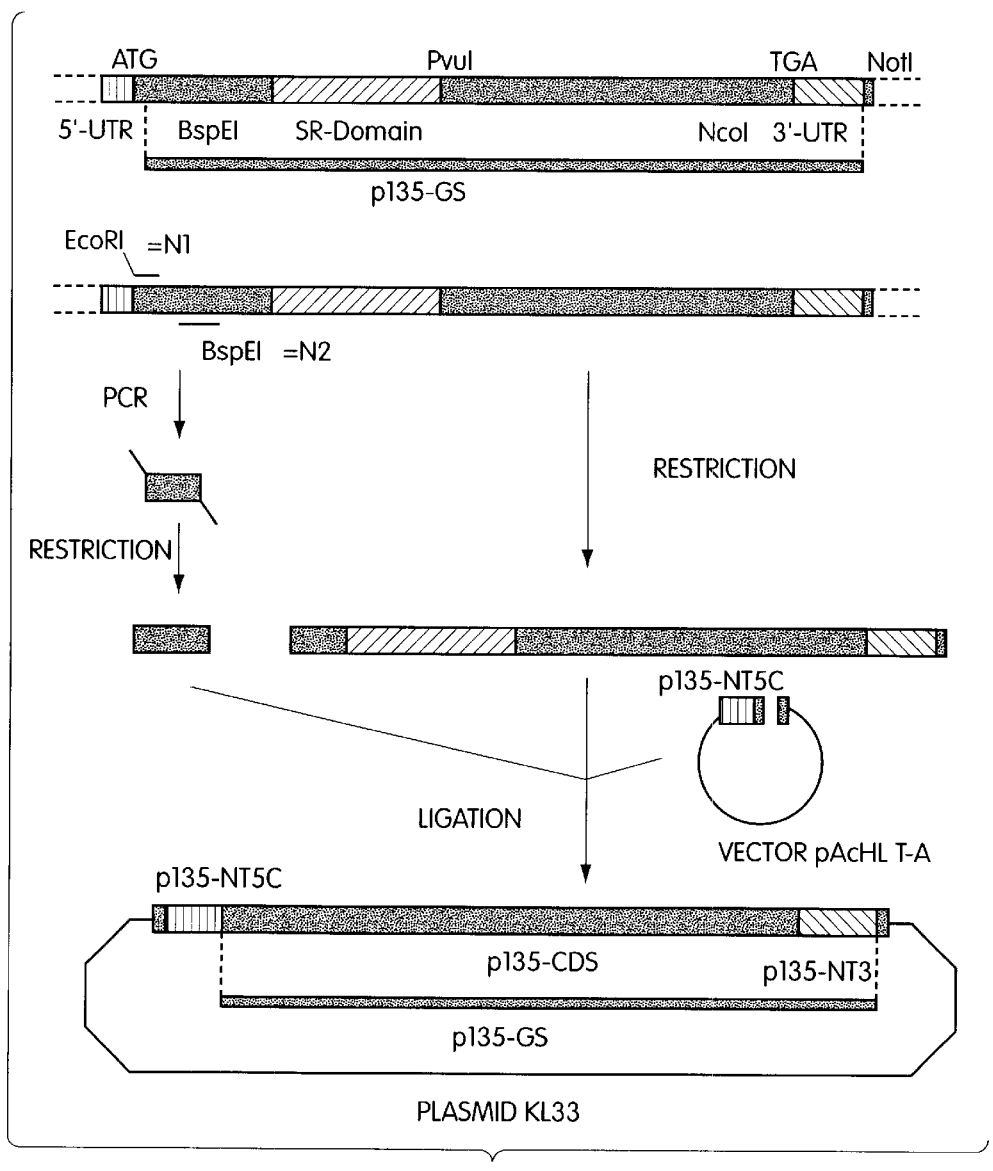

For the cloning of the plasmids (see also cloning scheme according to FIG. 5), the $E.coli$ strain TOP10 (Invitrogen®) was employed. For the exact fitting of the DNA, which codes for the p135 protein from EP-A-0 778 347, into the vector pAcHLT-A (Invitrogen®, see FIG. 8A), the N-terminus was amplified by means of PCR. For this, the oligodeoxynucleotides N 1:
5'-ATGAATTCGGGGACACCAGTGAGGATGCCTCG-3' (SEQ ID No. 3) and N2: 5'-CCGATAATGTCTGTCTTTCCGGATATT-3' (SEQ ID No. 4)

were used. After restriction cleavage with EcoRI and BspEI, the PCR fragment was employed together with the BspEI-NotI fragment of the cDNA of the p135 protein in a ligation reaction using the vector pAcHLT-A, which was linearized using the enzymes EcoRI and NotI. The plasmid KL33 thus obtained was confirmed by DNA sequencing. In the vector KL33 thus obtained the 5'-nontranslated region of the p135 cDNA is replaced by a so-called hexahistidine tag. This sequence section encodes a sequence of 6 histidine residues, which facilitate the detection and the purification of the fusion protein obtained. In the vector obtained, a short section of the 3'-noncoding DNA is moreover employed between the stop codon of the p135 cDNA and the terminator sequence specified by the vector pAcHLT-A.

In the next step, the plasmid KL33 was employed in a baculo-virus cotransfection. For this, $1 \times 10^6$ Spodoptera frugiperda ovarian cells SF21 cells (Invitrogen®) were transformed using 1 µg of Baculo-Gold DNA (Pharmingen®) and 2 µg of KL33 in 70 µl of serum-free medium containing 30 µl of lipofectin (Invitrogen®).

For the identification of recombinant baculoviruses, a plaque test was then carried out. Plaques isolated in this way were then incubated with $1 \times 10^6$ SF21 cells (Invitrogen®). The virus DNA was then isolated and employed as a matrix for a PCR. The oligodeoxynucleotides N1 and N2 were used in this test PCR. On analysis of the PCR batches in an agarose gel, a band of about 310 bp was seen only with recombinant baculoviruses but not with wild-type baculoviruses. For further confirmation, the clone KL33 was sequenced.

Well-washed SF21 cultures (about $2 \times 10^7$ cells) were infected with 200 µl of recombinant viruses in 75 cm² tissue culture flasks and incubated at 27° C. for 7 days in order to obtain sufficient BV33 stock for the subsequent protein expressions in Trichoplusia ni egg cells ("High Five cells", Invitrogen®). For further. replication, 3 ml of this stock solution were. incubated at 27° C. for 7 days in 100 ml of SF21 culture ($\approx 2 \times 10^8$ cells) in 250 ml spinners (Technomara®). The virus titer of the BV33 stock solution was determined using the virus titer assay.

For protein expression, 100 ml of HF cells in 1 l roller bottles were infected with BV33 virus stock at a cell density of $2 \times 10^6$/ml using an m.o.i. ("multiplicity of infection") of 3. Expression studies were carried out with the infected High Five cells in order to determine the optimum incubation period after infection. The yield of recombinant p135 was tested here by means of the band intensity in the SDS gel. After the corresponding incubation period, the cells were pelleted by centrifugation at 1500 g and purified to apparent homogeneity, i.e. it was only possible to detect one protein band visually. In this context, an infection period of about 72 hours turned out to be optimum. After disruption of the cells by passaging in a homogenizer, the proteins were dissolved in 8 M urea. The desired p135 protein was worked up to homogeneity from this solution. It was thus possible to obtain about 360 mg of protein from $1 \times 10^9$ "High Five cells".

Figure 2:
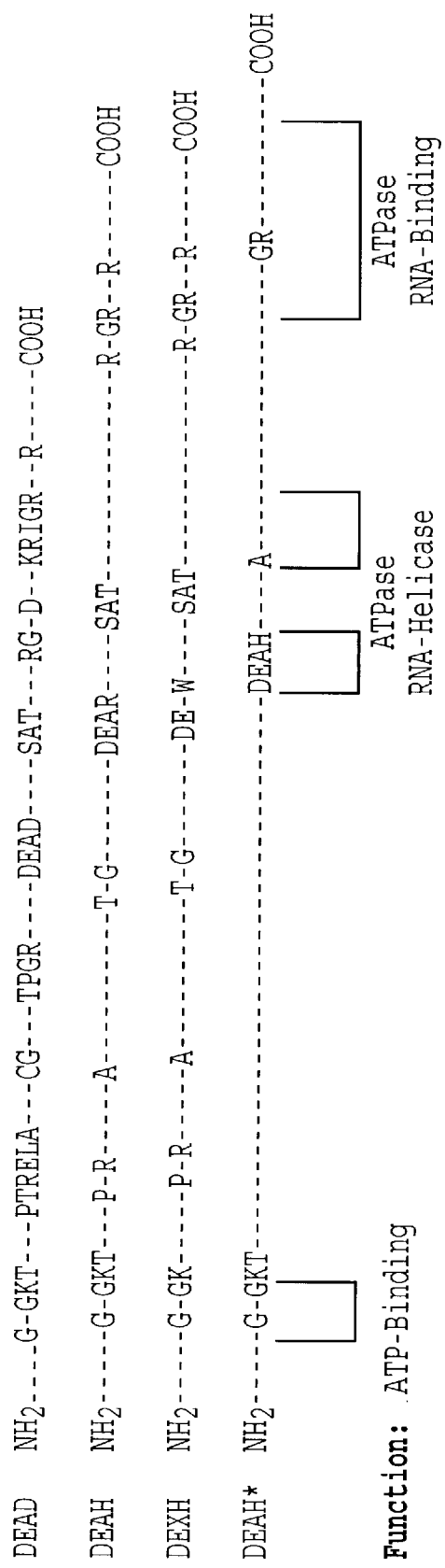
Figure 3A:
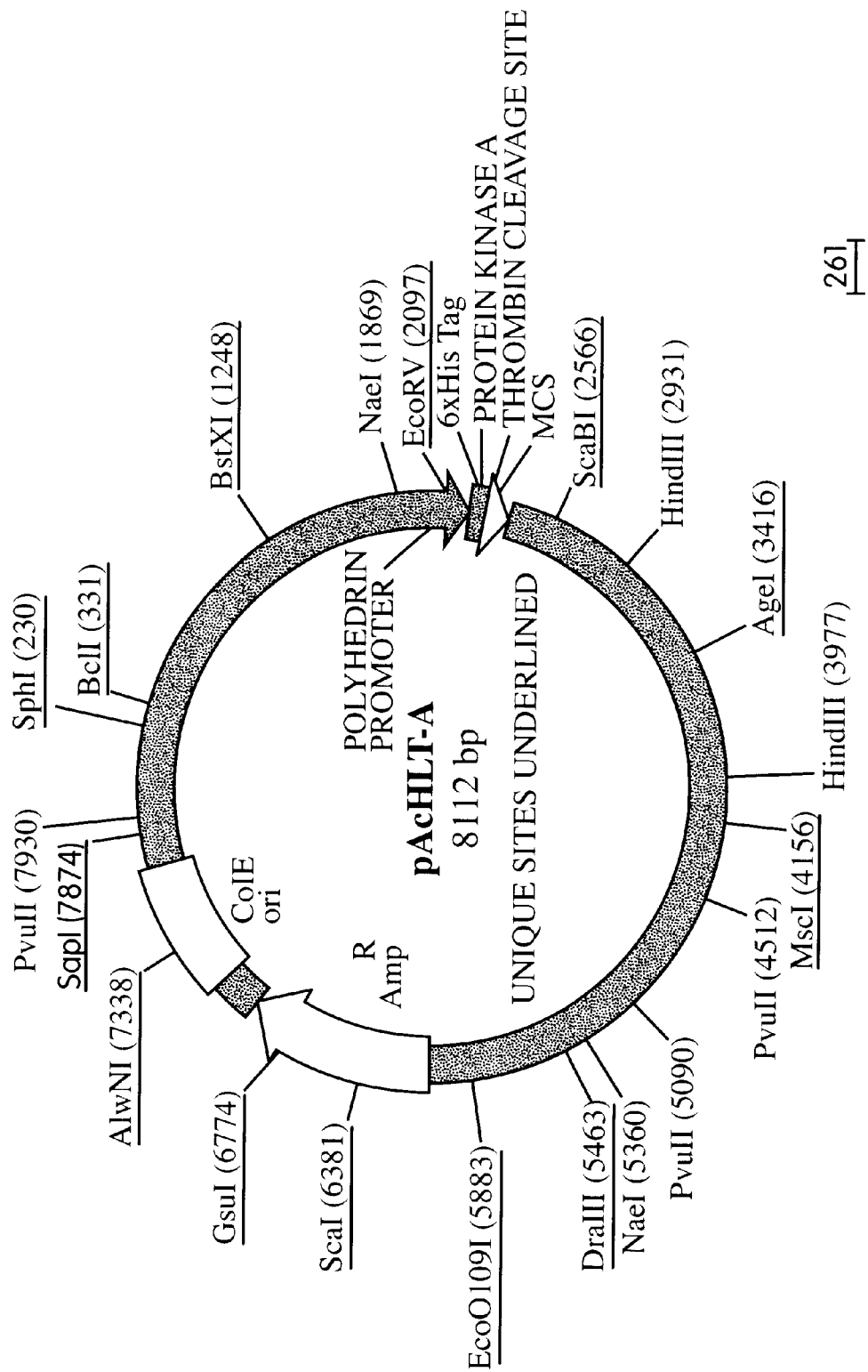
Figure 3B:
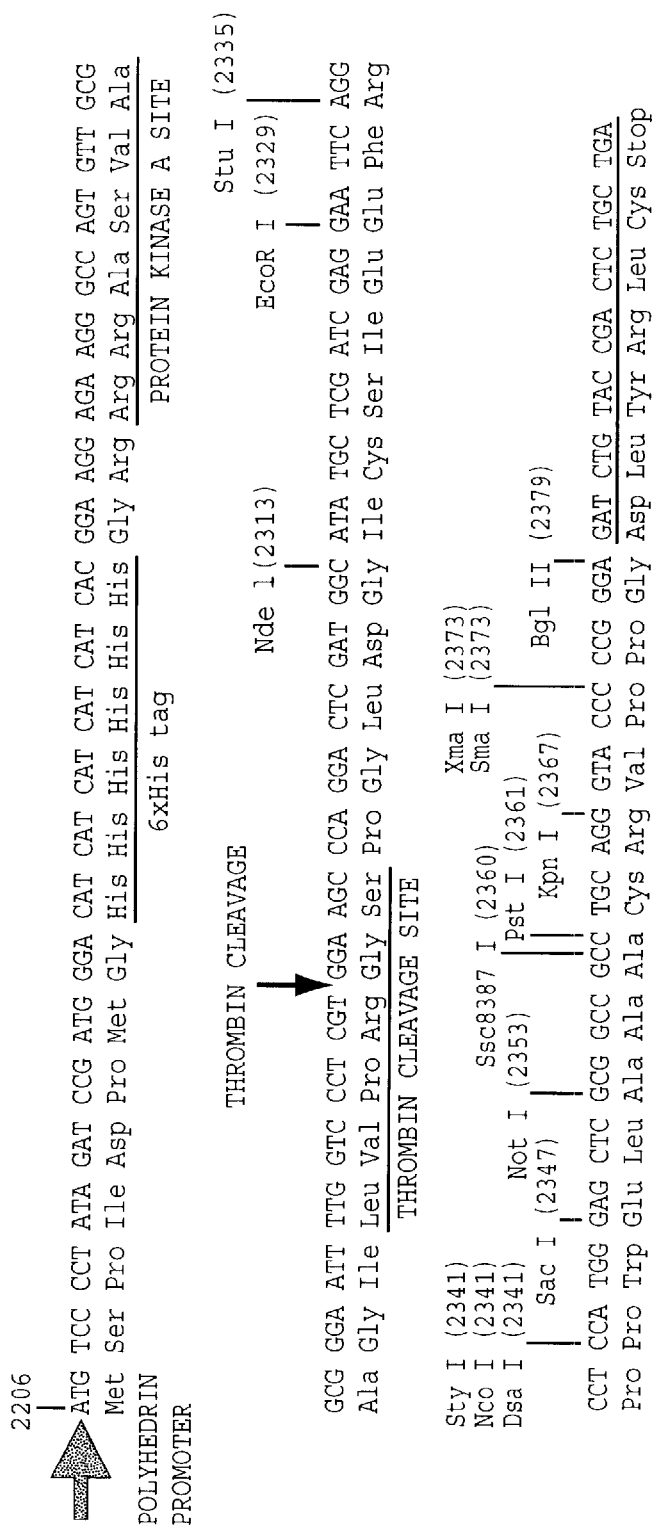
Figure 4A:
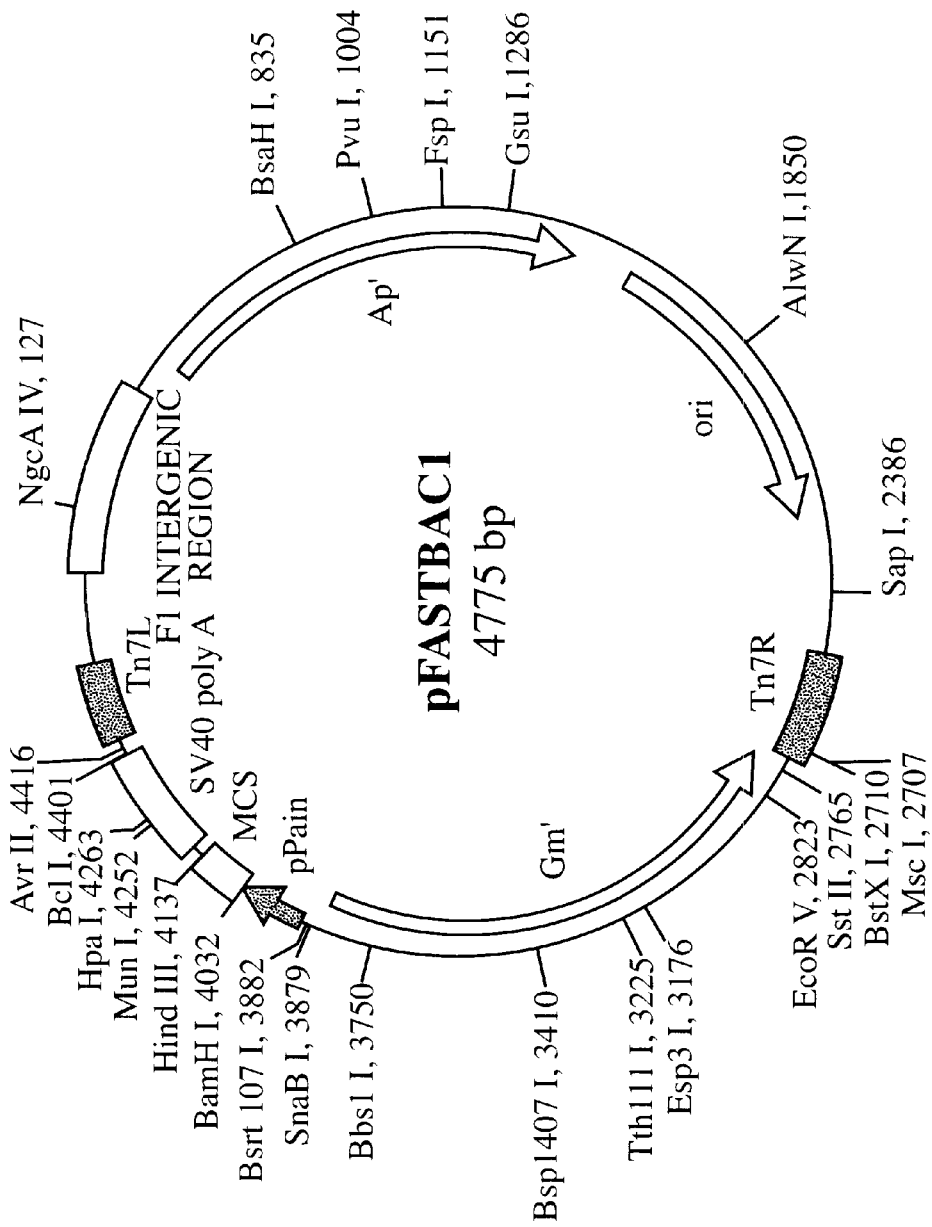

Example 2
Preparation of a Recombinant Baculovirus Expression Vector for the Secretory Expression of the p135 Protein For the secretory expression of the p135 protein, the p135 DNA was cloned (see FIGS. 4A and B) into the vector pFASTBAC1 (Gibco-BRL). The insulin signal sequence (p135-NT5S, SEQ ID No. 12) obtained from the hybridization of synthetic oligodeoxynucleotides and subsequent fill-in synthesis was first cloned in via the BamHI and EcoRI cleavage site of this vector. The vector FB1 thus obtained was then linearized by restriction with EcoRI and NotI. The vector linearized in this way was incubated with the sequence p135-GS from the vector KL33 in the presence of T4 ligase in a ligation batch. 100 µl of competent $E.coli$ DH10Bac cells (Gibco-BRL) were transformed using 1 ng of the clone FB2 thus obtained.

Recombinant bacmids can be identified here on account of their white coloration in blue-white screening. White colonies were streaked out on fresh plates in order to confirm the genotype. The recombinant bacmid DNA was then isolated in minilyses according to the instructions of the manufacturer (Gibco-BRL). Analogously to Example 1, it was confirmed by means of PCR with the oligodeoxynucleotides N1 and N2 that the recombinant bacmids contain the p135-DNA. For further confirmation, the clone BM33 was sequenced.

Using 5 µl of BM33 and 6 µl of Gibco-BRL CellFECTIN™ reagent of the recombinant bacmid BM33, $9 \times 10^5$ SF21 cells were transformed and incubated at 27° C. for 60 h. The recombinant viruses were replicated as described in Example 1.

After 72 h, the protein p135 was obtained in apparent homogeneity from the supernatants of infected HF cells (grown in a medium such as described in Example 1, but without FCS) by concentration of the supernatant and subsequent chromatographic purification. The work-up and purification was significantly facilitated by the secretion into the culture medium.

Comparison Example 1
Expression Experiments with the Bacterium *E.coli*

For expression in *E.coli,* two full-length constructs of p135-DNA with a different C terminus were cloned into the vector pGEX-4T-1 (Pharmacia®). The cloning was carried out by means of the restriction sites EcoRI and NotI of the vector. The fragments were recloned directly from the baculovectors. Construct Ec33-M contains p135-DNA without the native 3'-nontranslated sequence. In order to obtain this construct, a PCR was carried out using the oligodeoxynucleotides T1: 5'-TGA CAG TCG GAC TTA GTC CTA ACG CCG GCG ATA TGC ATG C-3' (SEQ ID No. 5) and T2: 5'-GCC TCT GCC ATG GAG GAG GAG ATG-3' (SEQ ID No. 6).

This fragment was exchanged after restriction with NcoI and NotI for the native C terminus of p135.

*E.coli* TOP10 cells (Invitrogen®) were transformed using the two clones Ec33-N and Ec33-M. After confirmation of the successful transformation by means of minilyses, the transformed cells obtained were grown to an OD800 of 0.7 and then induced using IPTG. After 1, 2, 3 and 4 hours, aliquots were analyzed for expression in the SDS-PAGE. It was not possible to detect any expression products.

Figure 7:
FIG. 7 shows a view of deletion constructs of p135.
Figure 7:

To check that the expression system functioned correctly, the deletion constructs D1 and D2 were expressed according to the above description (see FIG. 7). Using the construct D2, which is an internal fragment, it was possible to detect expression products.

Comparison Example 2
Expression Experiments Using the Yeast *Pichia pastoris*

Figure 6:
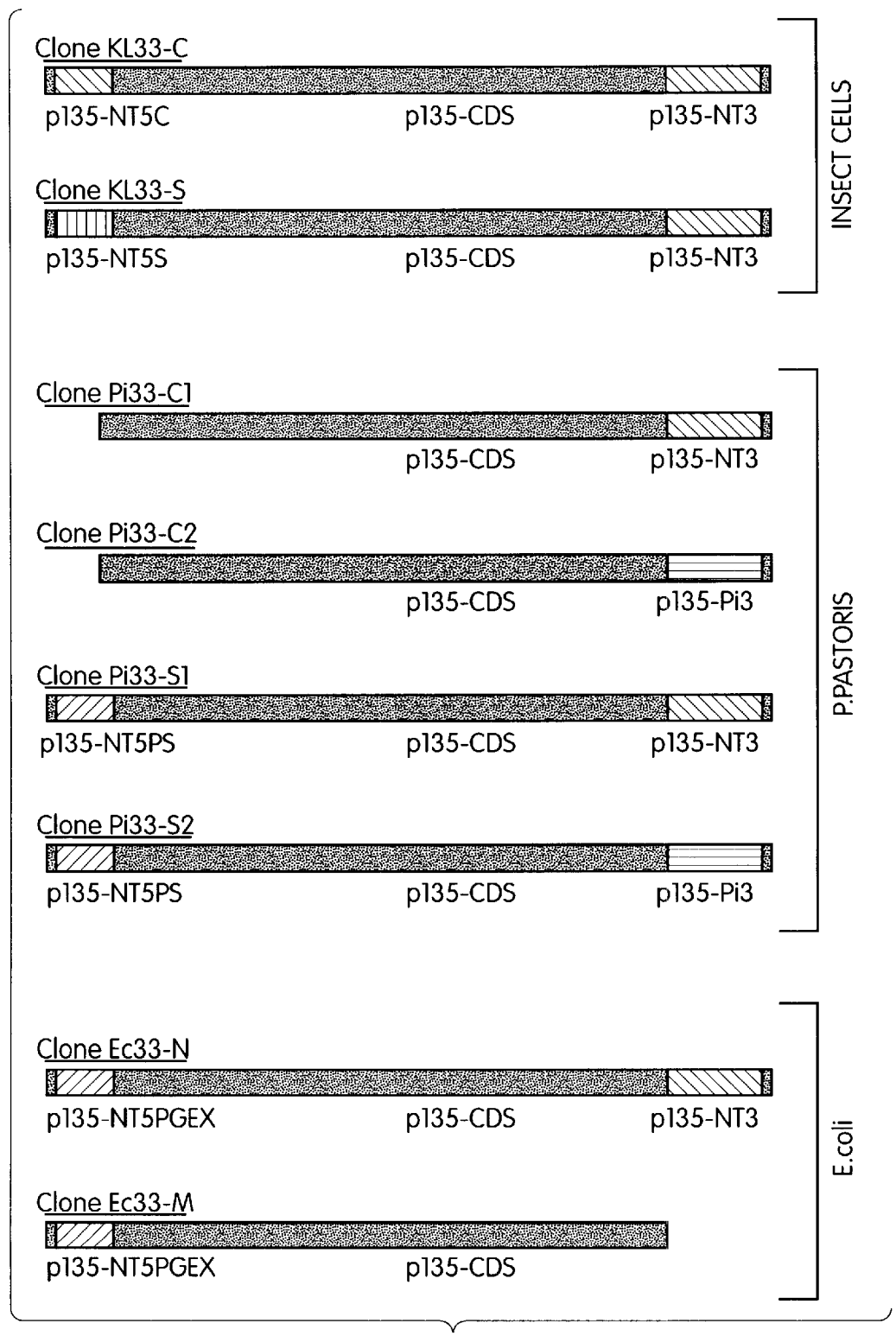
FIG. 6 shows a view of the gene constructs employed for the expression of the p135 protein in various host cells.

For expression in *P. pastoris,* two different full-length, constructs were cloned into the Pichia vectors pICZ A or pICZB (Invitrogen®, see also (http://www.invitrogen.com). The constructs (see FIG. 6) were isolated from the *E.coli* constructs Ec33-N and Ec33-M by restriction digestion and incorporated into the Pichia vectors by means of the cleavage sites EcoRI and NotI.

The *P. pastoris* cells of the strain KM71 were transformed according to the instructions of the manufacturer (Invitrogen®). For the analysis of the protein expression, the procedure was likewise according to the instructions of the manufacturer (Invitrogen®, No. K1740-01). It was not possible to detect any expression products.

To check that the expression system functioned correctly, the deletion clones D1 and D2 were expressed successfully according to the above description.

---

What is claimed is:

1. An insect cell vector comprising (a) a nucleic acid coding for a full-length protein from the DEAD protein superfamily and (b) a native 3'-noncoding region positioned at the 3' end of the coding region, wherein said vector, when introduced into a population of insect cells, causes accumulation of at least 300 mg of said protein per $10^9$ cells.

2. The vector of claim 1, wherein the 3'-noncoding region is at least about 50 nucleotides long.

3. The vector of claim 1, wherein the 3'-noncoding region is at least about 50 to about 450 nucleotides long.

4. The vector of claim 1, wherein the 3'-noncoding region is at least about 50 to about 400 nucleotides long.

5. The vector of claim 1, wherein the 3'-noncoding region contains a binding site for the CPSF protein, CstF protein, CF I protein, CF II protein, poly(A) polymerase, poly(A)-binding protein II (PAB II), or any combination thereof.

6. The vector of claim 1, wherein the 3'-noncoding region contains an AATAAA binding site, an ATTAAA binding site, a GT-rich element, a T-rich element, or any combination thereof.

7. The vector of claim 1, wherein the nucleic acid of (a) codes for a protein from the DEAD, DEAH, DEXH, or DEAH* protein family, or any combination thereof.

8. The vector of claim 1, wherein the nucleic acid of (a) codes for a protein having nucleic acid-binding activity, helicase activity, ATPase activity, or any combination thereof.

9. The vector of claim 1, wherein the nucleic acid of (a) codes for a human protein.

10. The vector of claim 1, wherein insect cell-specific regulatory nucleotide sequences are present at the 5' end of the nucleic acid of (a).

11. The vector of claim 1, wherein a polyhedrin promoter is contained at the 5' end of the nucleic acid of (a).

12. The vector of claim 1, wherein a polyhedrin-ATG translation initiation start site is contained at the 5' end of the nucleic acid of (a).

13. The vector of claim 1, wherein a nucleic acid is contained at the 5' end of the nucleic acid of (a) that codes for an oligopeptide of at least about 4 histidines, an oligopeptide of at least about 6 histidines, glutathione S-transferase, or any combination thereof.

14. The vector of claim 1, wherein a nucleic acid is contained at the 5' end of the nucleic acid of (a) coding for a protease cleavage site.

15. The vector of claim 1, wherein a nucleic acid is contained at the 5' end of the nucleic acid of (a) that codes for a signal sequence.

16. A process for the production of a protein from the DEAD protein family, said process comprising introducing a vector of claim 1 or a recombinant insect virus prepared by the process of claim 2 into insect cells or larvae, culturing the insect cells or larvae under conditions suitable for expressing the protein, and isolating the expressed protein, whereby said method results in accumulation of at least 300 mg of said expressed protein per $10^9$ cells.

17. The vector of claim 6, wherein the 3'-noncoding region contains a YGTGTTYY element.

18. An insect cell vector comprising (a) a nucleic acid coding for a protein from the DEAD protein superfamily and (b) a native 3'-noncoding region positioned at the 3'end of the coding region, wherein the nucleic acid of (a) codes for a protein which imparts to cells tolerance to leflunomide.

19. An insect cell vector comprising (a) a nucleic acid coding for a protein from the DEAD protein superfamily having a sequence according to SEQ ID No. 7.

20. An insect cell vector comprising (a) a nucleic acid comprising a sequence according to SEQ ID No. 8 coding for a protein from the DEAD protein superfamily.

21. The vector of claim 19, wherein the nucleic acid further comprises a sequence according to SEQ ID NO: 8.

22. The vector of claim 19, further comprising a native 3'-noncoding region positioned at the 3' end of the coding region.

23. The vector of claim 13, wherein a nucleic acid having the sequence according to SEQ ID No. 12 is contained at the 5' end of the nucleic acid of (a).

24. The vector of claim 14, wherein the protease cleavage site comprises a thrombin cleavage site having the sequence Leu-Val-Pro-Arg-Gly-Ser (SEQ ID No. 1), an FXa cleavage site having the sequence Ile-Glu-Gly-Arg (SEQ ID No. 2), or a combination thereof.

25. The vector of claim 15, wherein the signal sequence is selected from an insulin, bombyxin, human placental alkaline phosphatase, melittin, human plasminogen activator, or insect cell protein signal sequence, or is a leader sequence of a prokaryotic gene.

26. The vector of claim 15, or 25, wherein the nucleic acid coding for the signal sequence is a sequence according to SEQ ID No. 13.

27. A process for the production of recombinant insect viruses which code for a protein from the DEAD protein superfamily, said process comprising introducing a vector of claim 1 into insect cells together with insect virus wild-type DNA, and isolating the resulting recombinant insect viruses.

28. The process of claim 27, wherein the insect virus wild-type DNA is baculovirus DNA.

29. The process of claim 16, wherein the insect cells or larvae are infected with the recombinant insect virus.

30. The process of claim 27 or 16, wherein the insect cells are Spodoptera frugiperda cells.

31. The process of claim 29, wherein the infection period of the insect cells is about 40 to about 90 hours.

32. The process of claim 31, wherein the infection period of the insect cells is about 70 hours.

33. The process of claim 30, wherein the insect cells are Spodoptera frugiperda of ovarian cells.

34. An insect cell vector comprising (a) a nucleic acid coding for a protein from the DEAD protein superfamily and (b) a native 3'-noncoding region positioned at the 3'-end of the coding region, wherein a nucleic acid having the sequence according to SEQ ID NO: 12 is contained at the 5' end of the nucleic acid of (a).

35. An insect cell vector comprising (a) a nucleic acid coding for a protein from the DEAD protein superfamily and (b) a native 3'-noncoding region positioned at the 3'-end of the coding region, wherein a sequence according to SEQ ID NO: 13 is contained at the 5' end of the nucleic acid of (a).

36. The vector of claim 34 or 35, wherein the nucleic acid of (a) codes for a protein having nucleic acid-binding activity, helicase activity, ATPase activity, or any combination thereof.

37. The vector of claim 34 or 35, wherein the nucleic acid of (a) codes for a protein which imparts to cells tolerance to leflunomide.

* * * * *

UNITED STATES PATENT AND TRADEMARK OFFICE
CERTIFICATE OF CORRECTION

| | | |
|---|---|---|
| PATENT NO. | : 6,582,691 B1 | Page 1 of 1 |
| APPLICATION NO. | : 09/601537 | |
| DATED | : June 24, 2003 | |
| INVENTOR(S) | : Gallert et al. | |

It is certified that error appears in the above-identified patent and that said Letters Patent is hereby corrected as shown below:

References Cited, Foreign Patent Documents: "WO 96/18157" should be
--WO 93/18157--.

Column 6, line 50: "desired:amino acid" should be --desired amino acid--.

Column 8,
Line 9: "further. replication" should be --further replication--; and
Line 10: "were. incubated" should be --were incubated--.

Claim 16, column 33, line 53: "process of claim 2" should be
--process of claim 27--.

Signed and Sealed this

Twenty-fifth Day of September, 2007

JON W. DUDAS
*Director of the United States Patent and Trademark Office*